(12) United States Patent
Zhan et al.

(10) Patent No.: US 11,782,176 B2
(45) Date of Patent: Oct. 10, 2023

(54) BAD DETECTOR CALIBRATION METHODS AND WORKFLOW FOR A SMALL PIXELATED PHOTON COUNTING CT SYSTEM

(71) Applicant: CANON MEDICAL SYSTEMS CORPORATION, Otawara (JP)

(72) Inventors: Xiaohui Zhan, Vernon Hills, IL (US); Xiaochun Lai, Vernon Hills, IL (US); Yi Qiang, Vernon Hills, IL (US); Kevin Christopher Zimmerman, Vernon Hills, IL (US); Zhihong Ye, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 221 days.

(21) Appl. No.: 17/238,921

(22) Filed: Apr. 23, 2021

(65) Prior Publication Data
US 2022/0342098 A1    Oct. 27, 2022

(51) Int. Cl.
*G01T 7/00*    (2006.01)
*G01N 23/046*    (2018.01)
*A61B 6/00*    (2006.01)

(52) U.S. Cl.
CPC .......... *G01T 7/005* (2013.01); *G01N 23/046* (2013.01); *A61B 6/585* (2013.01); *A61B 6/586* (2013.01); *G01N 2223/303* (2013.01)

(58) Field of Classification Search
CPC .......... G01N 23/046; G01N 2223/419; G01N 2223/303; G01N 2223/50; A61B 6/032; A61B 6/482; A61B 6/4241; A61B 6/585; A61B 6/586; A61B 6/542; A61B 6/5282; A61B 6/5205; A61B 6/484; A61B 6/4266; A61B 6/4028; A61B 6/4007; A61B 6/06; A61B 6/544; A61B 6/4429; A61B 6/4014; A61B 6/4233; A61B 6/4085; A61B 6/487; A61B 6/5258; A61B 6/583; A61B 6/4291; A61B 6/4035; A61B 6/5235; A61B 6/541; A61B 6/5217; A61B 6/584; A61B 6/4447; A61B 6/035; A61B 6/488; A61B 6/4488; A61B 6/58; A61B 6/54; A61B 6/461;
(Continued)

(56) References Cited

U.S. PATENT DOCUMENTS 11,092,701 B1 * 8/2021 Shahar .................... G01T 1/247
2004/0039919 A1   2/2004 Takayama et al.
(Continued)

FOREIGN PATENT DOCUMENTS

JP    2004-304751 A    10/2004

*Primary Examiner* — Irakli Kiknadze
(74) *Attorney, Agent, or Firm* — Oblon, McClelland, Maier & Neustadt, L.L.P.

(57) ABSTRACT

A method and apparatus for diagnosing and/or calibrating underperforming pixels in detectors in a small pixelated photon counting CT system utilizes a series of tests on image data acquired in-situ as part of a series of calibration scans in the CT system. Tests are performed on the acquired data to determine the existence of underperforming pixels within the detectors such that the information acquired by those pixels can be replaced by alternate data from surrounding pixels (e.g. by interpolation). The underperforming pixels are stored in "bad" pixel tables and may be specific to a type of image (e.g., spectral or counting) and a specific protocol.

21 Claims, 10 Drawing Sheets

(58) Field of Classification Search
CPC ..... G01T 7/005; G01T 1/1611; G01T 1/2985;
G01T 1/20184; G01T 1/242; G01T 1/24;
G01T 1/17; G01T 1/247; A61N 5/1067;
A61N 5/1071; A61N 5/1043; A61N
2005/1087; G06T 11/005; G06T
2211/412; G06T 7/10; G06T 7/0012;
G06T 11/003; G01V 5/005
USPC .............................. 378/207, 4, 19, 62, 98.8
See application file for complete search history.

(56) References Cited

U.S. PATENT DOCUMENTS

| | | | | |
|---|---|---|---|---|
| 2005/0017187 | A1* | 1/2005 | Petrick | H04N 5/32 348/E5.081 |
| 2006/0039599 | A1* | 2/2006 | Deykoon | G01T 1/2985 378/4 |
| 2008/0048124 | A1* | 2/2008 | Pang | A61B 6/482 250/363.04 |
| 2011/0002440 | A1* | 1/2011 | Gatten | G01V 5/005 378/57 |
| 2011/0293161 | A1* | 12/2011 | Yi | A61B 6/4233 382/131 |
| 2015/0087885 | A1* | 3/2015 | Boisseau | A61N 5/1067 600/1 |
| 2019/0266436 | A1* | 8/2019 | Prakash | A61B 6/586 |
| 2023/0011644 | A1* | 1/2023 | Zhao | A61B 6/542 |

* cited by examiner

FIG. 4A

| Board | Module | Pixel | Protocol |
|---|---|---|---|
| 1 | 2 | (5,6) | S1 |

FIG. 4B

| Board | Module | Pixel | Protocol |
|---|---|---|---|
| 1 | 2 | (5,6) | S1 |
| 2 | 3 | (1,1) | S2 |

FIG. 5A

| Board | Module | Pixel | Protocol |
|---|---|---|---|
| 2 | 12 | (12,10) | C1 |
| 3 | 16 | (16,16) | C2 |

FIG. 5B

| Board | Module | Pixel | Protocol |
|---|---|---|---|
| 2 | 12 | (12,10) | C1 |
| 3 | 16 | (16,16) | C2 |
| 3 | 16 | (16,16) | C1 |
| 3 | 16 | (16,17) | C1 |
| 3 | 16 | (16,18) | C1 |

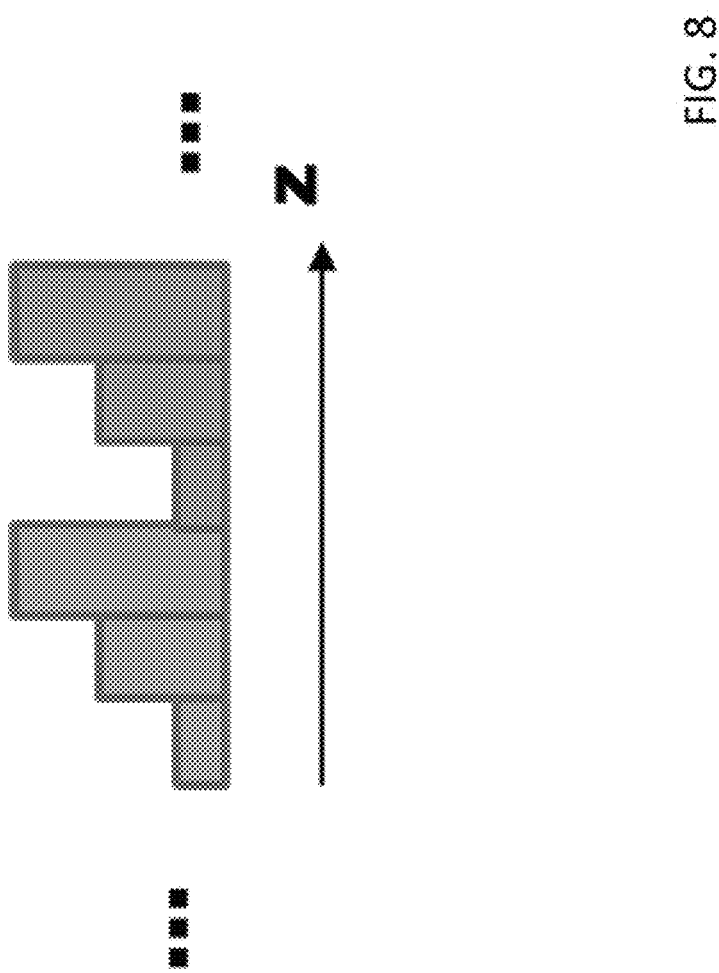

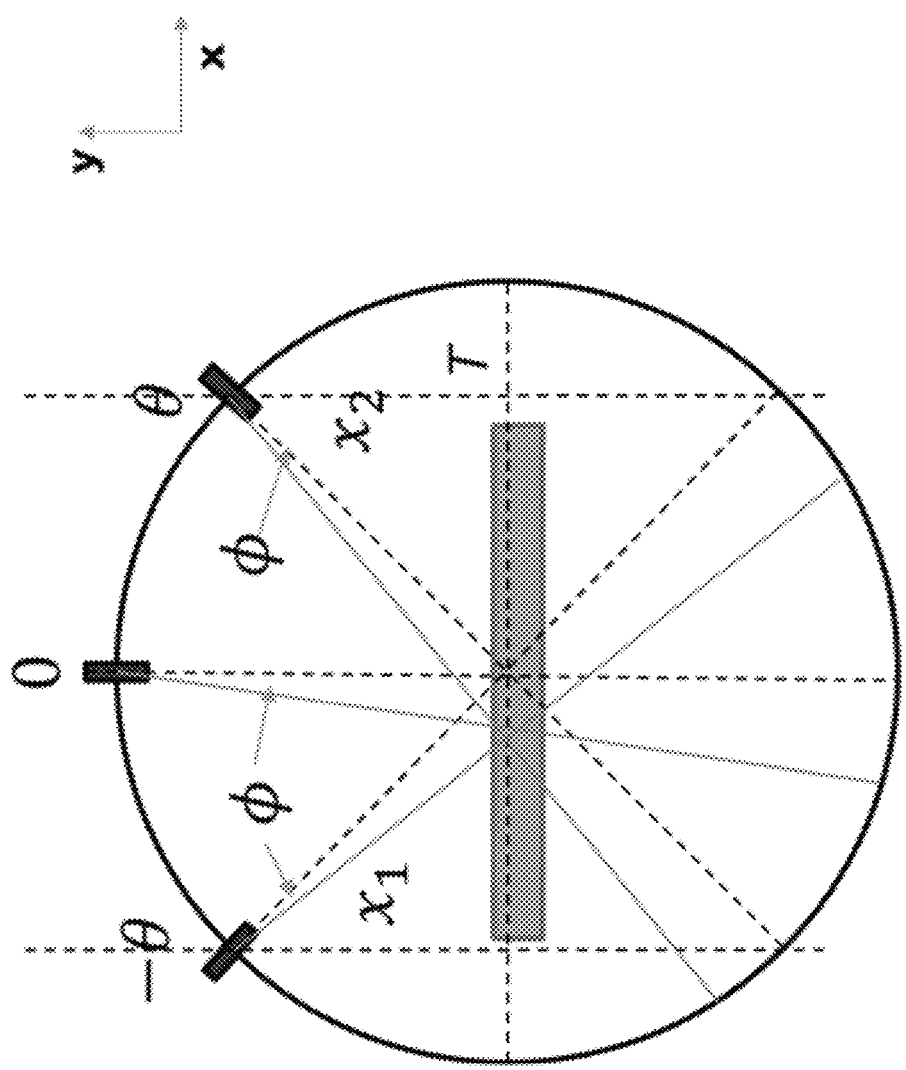

BAD DETECTOR CALIBRATION METHODS AND WORKFLOW FOR A SMALL PIXELATED PHOTON COUNTING CT SYSTEM

FIELD OF THE INVENTION

Embodiments described herein relate generally to an improved calibration system and method in a radiation detector, and in one embodiment to a method and apparatus for diagnosing and or calibrating bad detectors in a small pixelated photon counting CT system.

DESCRIPTION OF THE RELATED ART

Computed tomography (CT) systems and methods are widely used, particularly for medical imaging and diagnosis. CT systems generally create projection images of one or more sectional slices through a subject's body. A radiation source, such as an X-ray source, irradiates the body from one side. A collimator, generally adjacent to the X-ray source, limits the angular extent of the X-ray beam, so that radiation impinging on the body is substantially confined to a planar region (i.e., an X-ray projection plane) defining a cross-sectional slice of the body. At least one detector (and generally many more than one detector) on the opposite side of the body receives radiation transmitted through the body in the projection plane. The attenuation of the radiation that has passed through the body is measured by processing electrical signals received from the detector. In some implementations a multi slice detector configuration is used, providing a volumetric projection of the body rather than planar projections.

Typically the X-ray source is mounted on a gantry that revolves about a long axis of the body. The detectors are likewise mounted on the gantry, opposite the X-ray source. A cross-sectional image of the body is obtained by taking projective attenuation measurements at a series of gantry rotation angles, transmitting the projection data/sinogram to a processor via the slip ring that is arranged between a gantry rotor and stator, and then processing the projection data using a CT reconstruction algorithm (e.g., inverse Radon transform, a filtered back-projection, Feldkamp-based cone-beam reconstruction, iterative reconstruction, or other method). For example, the reconstructed image can be a digital CT image that is a square matrix of elements (pixels), each of which represents a volume element (a volume pixel or voxel) of the patient's body. In some CT systems, the combination of translation of the body and the rotation of the gantry relative to the body is such that the X-ray source traverses a spiral or helical trajectory with respect to the body. The multiple views are then used to reconstruct a CT image showing the internal structure of the slice or of multiple such slices.

Conventionally, energy-integrating detectors have been used to measure CT projection data. Now, photon-counting detectors (PCDs) present a feasible alternative to energy-integrating detectors. In a photon counting CT system, the semiconductor based detector using direct conversion is employed to resolve the energy of the individual incoming photons and generates measurement of multiple energy bin counts for each integration period. When a photon deposit energy in such a sensor materials (e.g. CdTe/CZT/Si), a charge cloud is formed and drifts toward the anode under the applied electric field. The detector energy response is largely degraded/distorted by charge sharing, k-escape, and scattering effects in the energy deposition and the following charge induction process, as well as electronic noise in the associated front-end electronics. Due to finite signal induction time, at high count-rate condition, pulse pile-up also distorts the detector energy response.

Due to sensor material non-uniformity and performance variations in the associated front-end electronics, the actual detector response of the integrated detector pixel is slightly different from each other. With proper calibration of the forward model, most of them can generate measurements that can provide a good pathlength estimate by solving the inverse problem. However, if the performance of the pixel is way beyond nominal, it is possible that its measurement can no longer be used, and needs to be discarded from further processing. Unlike the conventional scintillator based energy integration detectors (EID), a 'bad' photon counting detector pixel may exhibit the following issues: 1) Noisy counting background, 2) abnormal counting performance, 3) abnormal energy resolution, 4) nonlinear energy response, and 5) inaccurate energy threshold. As a result, the pixel may not be calibrated or corrected, and the screening criteria is more complicated than the conventional EID system.

While semiconductor-based PCDs provide unique advantages for spectral CT, they also create unique challenges. For example, due to pulse pile up, PCDs can exhibit a nonlinear response with respect to X-ray flux. Without correcting for nonlinearities and spectral shifts in the detector response, images reconstructed from semiconductor-based PCDs can have poorer image quality.

However, PCDs have many advantages including their capacity for performing spectral CT and the ability to divide the scan area into many smaller "pixels" of detectors for greater resolution. Spectral CT can be advantageous because it provides information regarding the change in X-ray attenuation as a function of the energies of the X-rays. Also, a photon counting CT system can generate counting images based on measurements of the total count of each detector pixel in an integration period. Compared to conventional CT based on EID, the measurements provide equal weighting of each registered photon which is more optimal for resolving different materials.

Another important application is spectral imaging, for which the measurement of multiple energy bin counts are used to resolve difference materials which may exhibit the same CT number in conventional images. For example, spectral CT is desirable because different materials, such as bone and water, exhibit different spectral absorption signatures, enabling a spectral resolved CT scan to be decomposed into material components.

SUMMARY

A method and apparatus for diagnosing and/or calibrating underperforming (or "bad") pixels in detectors in a small pixelated photon counting CT system utilizes a series of in-situ tests on image data acquired as part of a series of calibration scans. Tests are performed on the acquired data to determine the existence of underperforming pixels within the detectors such that the information acquired by those pixels can be replaced by alternate data from surrounding pixels (e.g., by interpolation). The underperforming pixels are stored in "bad" pixel tables and may be specific to a type of image (e.g., spectral or counting) and a specific protocol.

BRIEF DESCRIPTION OF THE DRAWINGS

The application will be better understood in light of the description which is given in a non-limiting manner, accompanied by the attached drawings in which:

FIGS. 4A and 4B are exemplary bad spectral pixel tables before and after a bad pixel detection process of FIG. 3.

FIGS. 5A and 5B are exemplary bad counting pixel tables before and after a bad pixel detection process of FIG. 3.

FIG. 8 shows an example of a calibration slab design where calibration slabs are lined up in a Z-direction along at least a portion of a patient couch or other movable mechanism within the detector field.

FIG. 10 is a schematic that shows how different X-ray tube locations can generate different path lengths for a slab scan during calibration.

DETAILED DESCRIPTION OF THE PREFERRED EMBODIMENTS

Reference throughout this specification to "one embodiment" or "an embodiment" means that a particular feature, structure, material, or characteristic described in connection with the embodiment is included in at least one embodiment of the application, but do not denote that they are present in every embodiment.

Thus, the appearances of the phrases "in one embodiment" or "in an embodiment" in various places throughout this specification are not necessarily referring to the same embodiment of the application. Furthermore, the particular features, structures, materials, or characteristics may be combined in any suitable manner in one or more embodiments.

This disclosure relates to a photon counting CT scanner system for material decomposition, said CT scanner system comprising one or more X-ray tubes that emit X-ray radiation, and an array of detector pixels for receiving the X-ray radiation propagating through a field of view of the CT scanning system.

Figure 1:
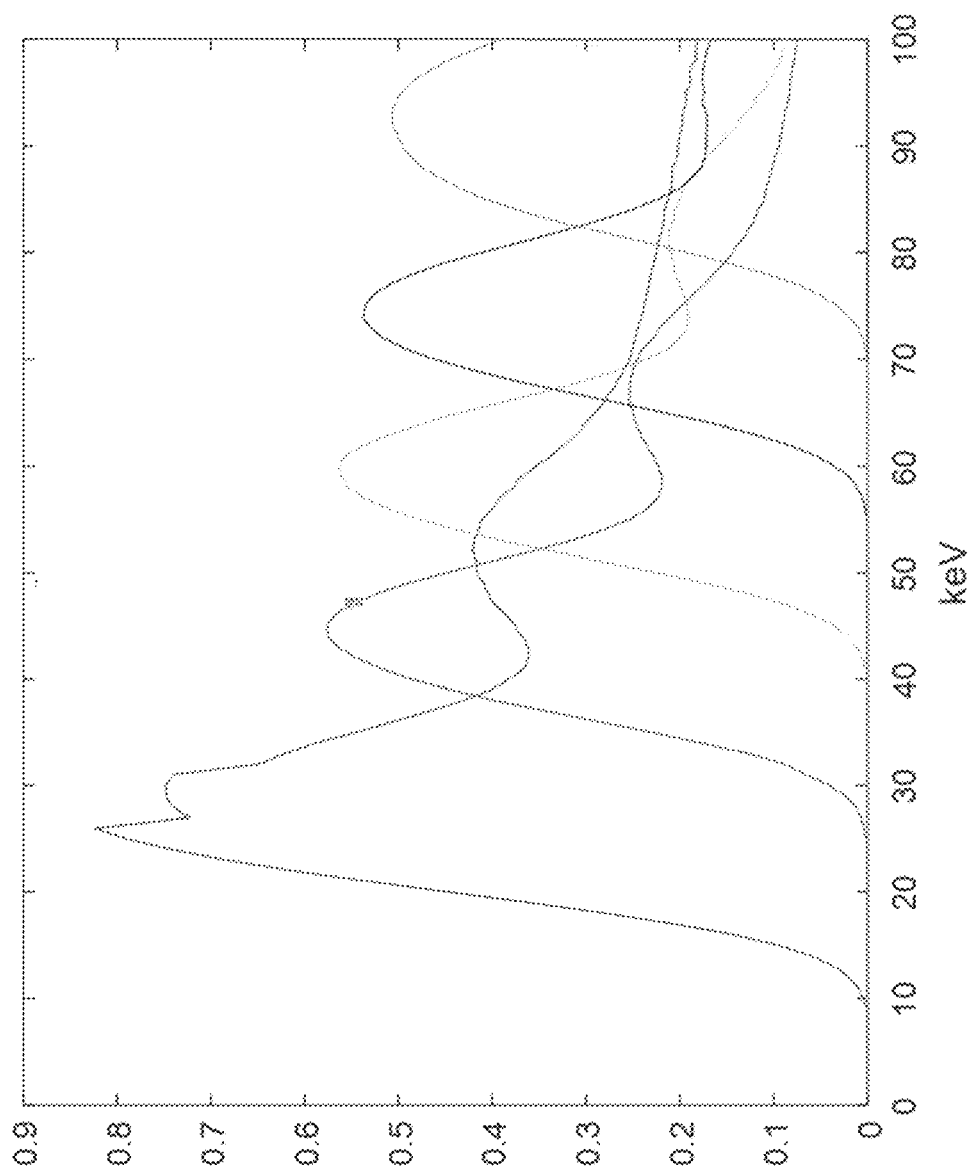
FIG. 1 shows an example of a PCD bin response function $S_b(E)$ for a photon counting detector with each curve representing an example function for each energy bin.

In a transmission measurement using a photon counting energy-resolving detector (PCD), the forward model can be formulated as below:

$$N_b(l_1,\ldots,l_M) = N_0 \times \int dE\, w(E) S_b(E) \exp(-\Sigma \mu_m l_m), \quad (1)$$

where $S_b(E)$ denotes the bin response function defined as $S_b(E) = \int_{E_{bL}}^{E_{bH}} R(E, E') dE'$, where $R(E,E)$ is tire detector response function, and $E_{bL}$ and $E_{bH}$ are the low and high energy threshold of each counting bin. FIG. 1 shows an example model of a typical $S_b(E)$ function for a PCD, where a long tail above the energy window is induced by charge sharing, k-escape and scattering effect. The low energy tail is mostly due to the finite energy resolution from the associated electronic noise. $N_0$ is the total flux from an air scan, $\mu_m$ and $l_m$ are the $m^{th}$ basis material linear attenuation coefficient and path length, $w(E)$ is the normalized incident X-ray spectrum. In practice, both $w(E)$ and $S_b(E)$ are not exactly known, and they can be combined as one term, $S_{wb}(E) = w(E) S_b(E)$, called thereafter the weighted bin response function. If $S_{wb}(E)$ can be calibrated through measurements, the decomposition problem at low flux condition can be well solved.

For a high flux scan condition (e.g., a few percent of pulse pileup), pulse pileup introduces additional spectral distortion in the measurement. One way to correct for the pileup effect is to introduce additional correction terms. The forward model becomes:

$$N_b(l_1,\ldots,l_M) = N_0 \int dE\, S_{wb}(E) * P_b(E, N_b, N_{tot}) \exp(-\Sigma \mu_m(E) l_m).$$

where $P_b$ is a parameterization based on the photon energy, the measured bin counts and the total count.

For a counting image measurement, the total count is used instead of the individual bin count, the forward model can be adjusted as:

$$N_{tot}(p) = N_0 \int dE\, S_w(E) * P(E, N_{tot}, p) \exp(-\int \mu(E,r) dl),$$

where $\mu(E, r)$ is the local attenuation coefficient, and projection integral $p = \int \mu(E, r) dl$, $S_w(E)$ is now the total count weighted bin response function, and $P(E, N_{tot})$ is the total count pileup correction term which is a function of $E$, $N_{tot}$, p.

Due to the complexity of the photon counting detector sensor fabrication, front-end electronics performance and packaging process, underperforming pixels (also referred to as "bad" pixels) can exhibit issues such as high background count, counting non-uniformity, abnormal energy response, instability, etc. As a result, the pixel either cannot produce valid measurement with a stable forward model, or has a forward model that is insensitive to the pathlength information, and either way, it should be excluded in the scanning measurements or later on processing. As noted in greater detail below, an underperforming pixel does not have to be completely inactive to be considered a "bad" pixel, and in Ent an underperforming detector pixel may be considered "bad" for a first imaging protocol and not a second imaging protocol.

Figure 2:
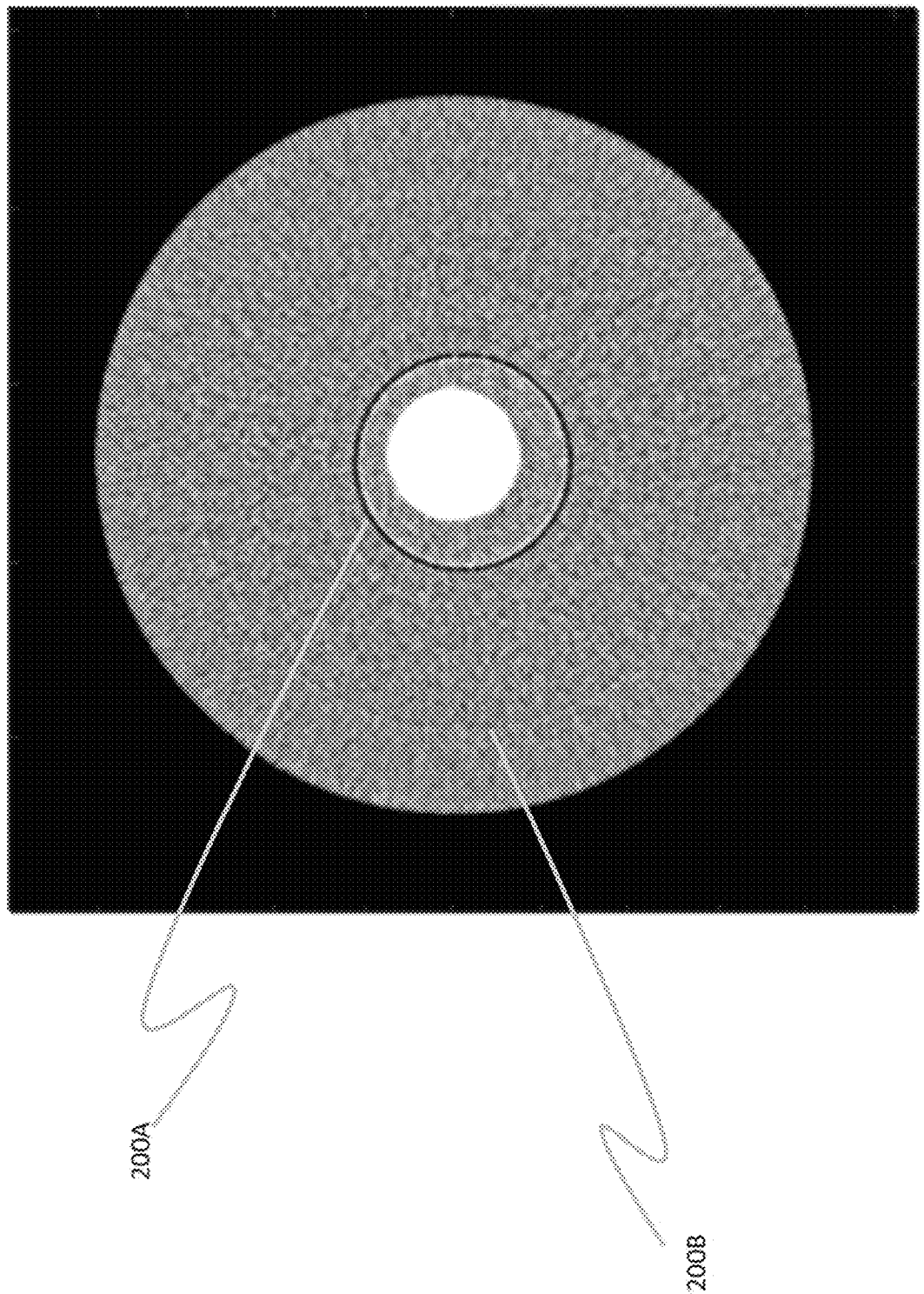
FIG. 2 is an exemplary image of showing an effect of a bad photon counting detector used during an image capture process.

For the counting mode, the image quality is sensitive to the total counts in each projection, and the energy information of the registered photon is not needed. For the spectral mode, not only the registered count needs to be accurate, the registered energy bin of each photon is also important. Therefore, the bad pixel criteria for different imaging modes could be different. Without a proper identification of the bad pixels and correction in the data processing, the resulted images would have visible ring/band artifact that affect the diagnosis, such as illustrated in FIG. 2 where there are visible ring artifacts 200A and 200B.

It is also very common for detectors to experience degradation with accumulated usage, and new bad pixels would come up from time to time. Those new bad pixels need to be captured for consistent image quality during the system lifetime.

Figure 3:
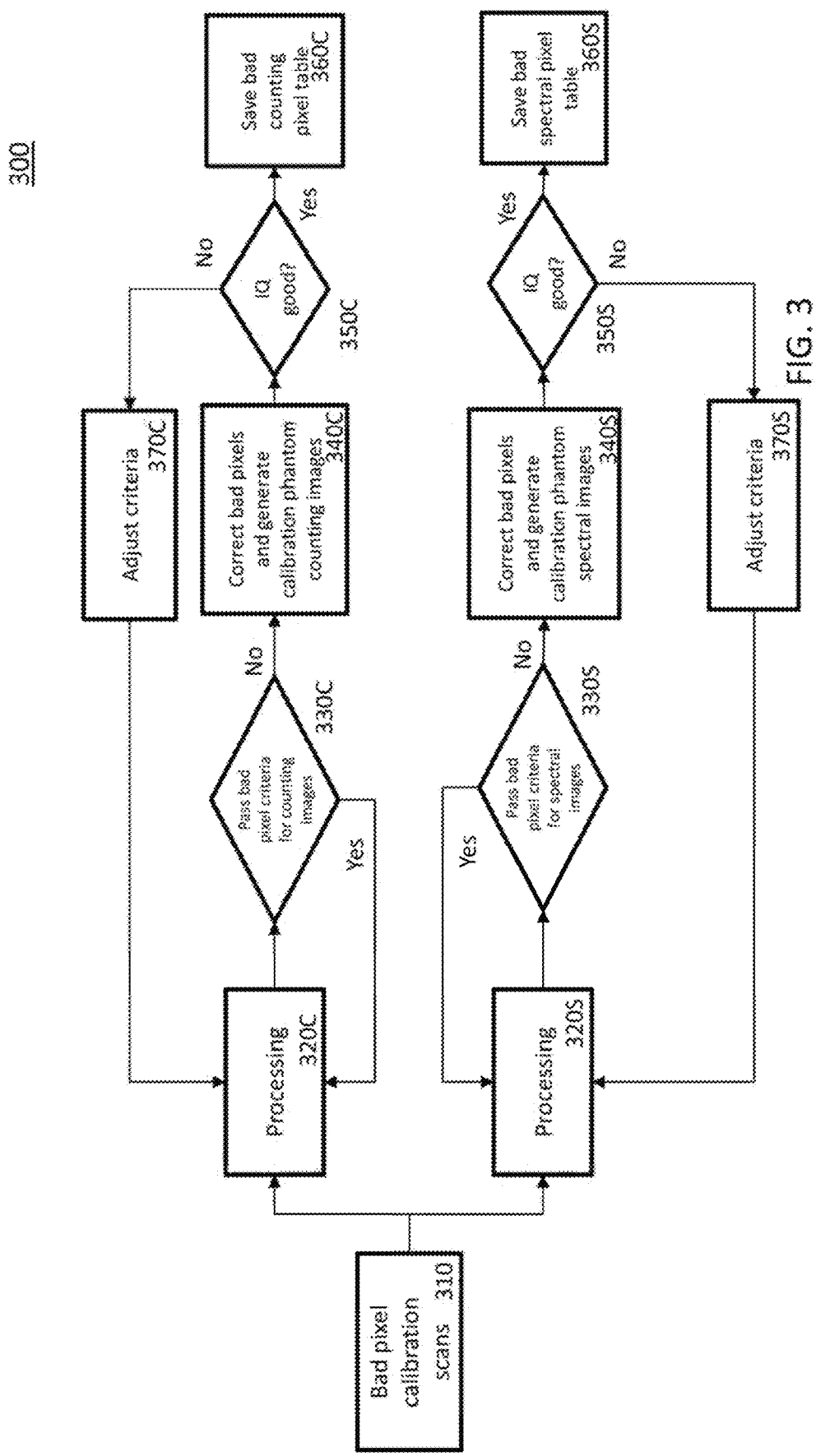
FIG. 3 is a flowchart showing an in-situ process of determining if a counting photodetector is properly operating for the capture of spectral images and counting images.

FIG. 3 is a flowchart showing an in-situ process 300 of determining if a counting photodetector is properly operating for the capture of spectral images and counting images. In step 310, a series or bad pixel calibration scans are performed, and the processing of those scans is then performed to assess acceptability, of the detectors for spectral images and counting images. For example, a low noise image from a uniform calibration phantom can be used to identify the bad pixels.

As shown in FIG. 3, the processes for spectral images and counting images are essentially independent, and the processes can be performed serially or in parallel, and, when in parallel, the processes can even be performed on separate computing systems.

Turning to the processing of the acceptability of the detectors for spectral images, after the calibration scans 310 has acquired spectral-oriented data, the control of the process passes to step 320S where the spectral-oriented data is processed according to a number of tests. In general, for each test that the testing system performs in step 320S, control is passed to step 330S to determine if the detectors were acceptable under the conditions of the test. If the detectors were acceptable, then control passes back to step 320S if there are remaining spectral tests or terminates (or transfers control to the counting tests) if there are no more remaining spectral tests.

If step 330S determines that a spectral test did not pass, then control passes to step 340S where the system attempts to isolate the bad pixels in the faulty detector and correct for the bad pixels. The system further generates another calibration phantom spectral image having isolated the bad pixels and tests the resulting image quality (IQ) in step 340S. If the image quality is sufficiently good, then the system can update a bad spectral pixel table (e.g., as shown in FIGS. 4A and 4B) in step 360S which the system can use during the processing of subsequent spectral images. Control can then pass back to step 320S for the next spectral processing test.

If step 350S determines that the image quality is not good enough, then the processing criteria may have to be adjusted as discussed in greater detail below), and control passes to step 370S before returning to steps 320S for any remaining spectral tests.

After or in parallel with the processing of the acceptability of the detectors for spectral images, the system processes the acceptability of the detectors for counting images. That processing starts in step 320C where the counting-oriented data is processed according to a number of tests. In general, for each test that the testing system performs in step 320C, control is passed to step 330C to determine if the detectors were acceptable under the conditions of the test. If the detectors were acceptable, then control passes back to step 320C if there are remaining counting tests or terminates if there are no more remaining counting tests.

If step 330C determines that a counting test did not pass, then control passes to step 340C where the system attempts to isolate the bad pixels in the faulty detector and correct for the bad pixels. The system farther generates another calibration phantom counting image having isolated the bad pixels and tests the resulting image quality (IQ) in step 340C. If the image quality is sufficiently good, then the system can update a bad counting pixel table (e.g., as shown in FIGS. 5A and 5B) in step 360S which the system can use during the processing of subsequent counting images. Control can then pass back to step 320C for the next counting processing test.

If step 350C determines that the image quality is not good enough, then the processing criteria may have to be adjusted, and control passes to step 370C before returning to steps 320C for any remaining counting tests.

Figure 6:
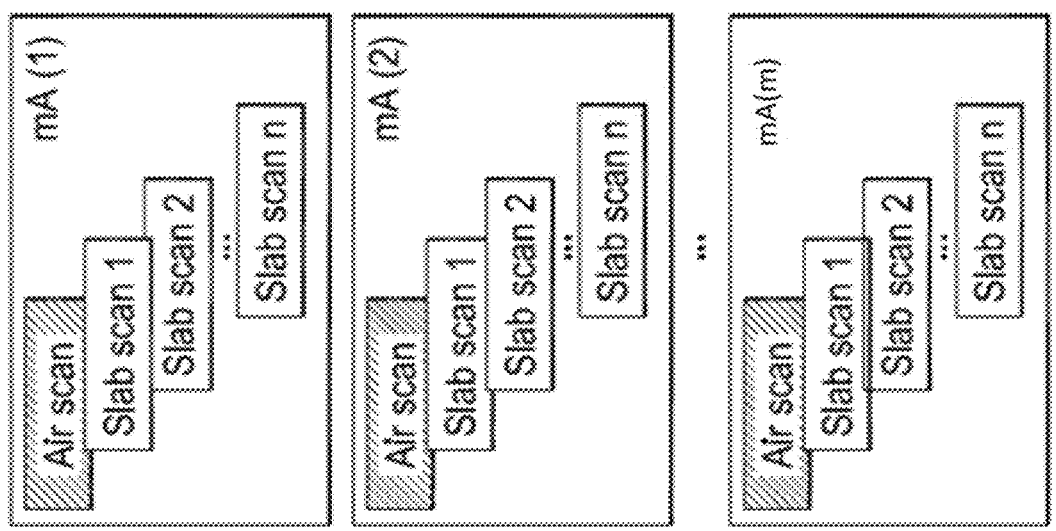
FIG. 6 shows a schematic of a calibration technique for performing a series of calibration scans according to one aspect of FIG. 3.

When performing bad pixel calibration scans in step 310, the system preferably performs a series of calibration scans that covers the operational scan settings needed to identify abnormal detector response for each pixel. There can be multiple sets of scans at different protocols which include the configuration of kVp, mA, bowtie configuration, collimation, rotation speed, integration time, etc. The scans can include any combination of at least one of:

1) a group of air scans of different intensities (e.g., from low to high mA (as shown in FIG. 6) or from high to low mA) to test the detector counting characteristics. In order to maintain a more uniform flux exposure in the detection field of view, bowtie filter can be removed for such scans.

2) a group of scans using slabs of different materials and thicknesses (as shown ire FIG. 8) using different intensities (e.g., from low to high mA or vice versa) to test the detector spectral response characteristics. The normalized bin count can be used in the analysis to screen out the pixels with abnormal spectral response.

3) a dark scan (no X-ray) to test the detector counting background for noise assessment.

4) a group of air scans at multiple intensity settings with time duration from seconds to mins and across multiple hours or multiple days.

In addition to testing whether there are bad pixels according to the criteria of steps 330C and 330S, it is possible to test system wide criteria as well. A number of exemplary criteria are described below that are system wide, counting or spectral, but the testing methods described herein are not limited to the explicitly recited criteria.

Criterion 1

For example, according to exemplary Criterion 1, a pixel can be considered bad if its background count rate is too high ($N_{bt} > N_{offset}$) for any of die bin counts.

Criterion 2

Turning to exemplary Criterion 2 to be used in step 330C, the system can assess counting performance based on any combination of at least one of:

(a) the count rate is too low or too high at a given flux $N_i > N_{high}(mA)$ or $N_i < N_{low}(mA)$; and $$\frac{N_i(mA)}{N_i(mA_0)} > r_{high}(mA) \text{ or} \qquad (b)$$

$$\frac{N_i(mA)}{N_i(mA_0)} < r_{low}(mA),$$

where $N_i(mA)$ is the measured counts of the pixel at a specific mA flux and $N_i(mA_0)$ is the same pixel measured counts at the lowest mA flux, where the pulse pileup effect is minimized.

Criterion 3

Turning to exemplary Criterion 3 to be used in step 330S, the system can assess spectral performance by determining whether a spectral response is abnormal by determining whether:

$$\frac{N_{bi}}{N_{tot}} > T_{hgh}(mA, \mu_j L_j) \text{ or}$$

$$\frac{N_{bi}}{N_{tot}} < T_{low}(mA, \mu_j L_j),$$

where $N_{bi}$ is the individual bin count in each slab/filter/mA measurement, $N_{tot}$ is the total count, and $T_{high}$ and $T_{low}$ are two bin response thresholds for the normalized bin count in each slab/filter/mA measurement j with attenuation $\mu_j L_j$. The bin response thresholds can be determined to be 5-10% below and above the mean value of all the pixels that passes the system wide criteria and the counting criteria.

Criterion 4

Additional testing in steps 330C and 330S can include performing a residual least square error to select the abnormal pixels after having calibrating the forward model for the counting and spectral mode measurement. A typical criteria can be derived with the calibrated forward model $S=(N_{bi}^{j}-f_{bi}^{j}(\mu_{j}L_{j}))^2$. j is the slab pathlength index, i is the pixel index, and b is for the individual energy bin. The mean value and standard deviation of S can be calculated for a group of neighboring pixels, and any pixel with S larger than x standard deviation can be marked as bad pixels (e.g., where x is between 3 and 5). The scans used for the forward model calibration can be a few air scans in combination of multiple slab scans with known material and thickness at different mA settings, as described in greater detail below with respect to FIG. 6. This tests whether the forward model can be accurately calibrated with the selected forward model, and it can be used standalone or in combination with any of the above-noted Criteria 1-3 for bad pixel screening. One example: if a pixel fails the least square error test, it can be labeled as bad pixel even it passed Criteria 1-3. And if it passed the least square error test, but failed Criteria 1-3 outstandingly, it can still be characterized as bad pixel. If it passed the least square error test but only failed Criteria 1-3 marginally, it may still be characterized as good pixel before the first IQ test with the uniform Phantom (step 4).

Criterion 5

At low flux conditions when the pileup effect is not prominent, as part of a noise test, the counting performance of the detector can be approximated as a Poisson distribution. For an ideal Poisson distribution, the variance of the counts is equal to the mean value of the counts. One can use the ratio of the counting variation and the mean to discriminate the pixels with outstanding noise. An example, of the criteria can be defined as:

$$\frac{\text{Var}(N_i)}{\text{Mean}(N_i)} < R$$

Where $N_i$ is the total counts of the pixel for view i with the typical integration time as the main operational scans, and the sample size large enough for such evaluation. The testing protocol should satisfy low flux condition where $n\tau<y$, with n being the incident count rate per pixel, and $\tau$ as the effective counting deadtime. y can be selected between 0.01-0.1, indicating the pileup events is less than 1% or 10% the total incident counts. R can be selected between 1.5 to 2, depending on the value y.

Criterion 6

For all the detection flux related criteria, the thresholds can be defined differently for edge/corner and the center pixels, if the size of the edge/corner pixels are different from the center pixels. An exemplary method uses pixel area normalized value for $N_{offset}$, $N_{high}$, $N_{low}$.

Criterion 7

The criteria for different scan protocols may also vary as the calibration scans used to determine the bad pixels can be different. One example is that for high flux protocols, some pixels may start to fail the counting performance test but pass the low flux counting performance test, and can be treated as good pixel for operational scans using low flux.

Criterion 8

After correcting X-ray flux fluctuation over time (with a valid reference detector reading), a detector pixel should have a stable counting output with fluctuation caused by statistic noise during the scan. Any metrics that can measure the detector detected counts drifting from this constant value overtime can be used to identify the pixels that have temporal stability issues. For example, as part of a repeatability or reliability test, maximum count deviation from mean or median value can be assessed, and/or a white noise test can be performed. If the metric is beyond the preset range, the pixel will identified as a bad pixel. Furthermore, the detected counts between one acquisition to another cross hours and days should be consistent within statistical error. If the detected counts at any acquisition is significantly different from the preset range, the pixel will be identified as a bad pixel.

In steps 340C and 340S, after bad pixels are identified based on previously defined criteria, the readings of these pixels are interpolated. The interpolation can be designed in the raw count measurement domain (in step 340C), where each bin count is interpolated from the neighboring pixels. The interpolation can also be designed in the basis material sinogram domain (as in step 340S), where the estimated path lengths of those pixels are interpolated from its neighbors.

In steps 340C/370C and 340S/370S, a uniform phantom with water or other tissue mimicking materials that are of common interest can be used to test and adjust the bad pixel criteria. After the initial criteria is set and bad pixels are interpolated, the phantom image can be generated based on the calibrated forward model. If there are visible rings (as in FIG. 2) with the initial criteria in the phantom image, the criteria will be tightened for the next iteration, e.g. use smaller x value in Criterion 4, until the ring artifact is minimized. Then the criteria is fixed at the value of the final iteration.

Although not shown in the figures, it also is possible to loosen the criteria if there are no visible rings in the image. In such a case where the current criteria are sufficient to meet image quality requirements, a parameter of one or more criteria may have room to be relaxed, (e.g., by using a larger x value in Criterion 4), and repeat the screening—interpolation—phantom image process can be repeated until, rings become present. Then the parameters of the criteria are fixed at the value of the previous iteration.

Figure 9A:
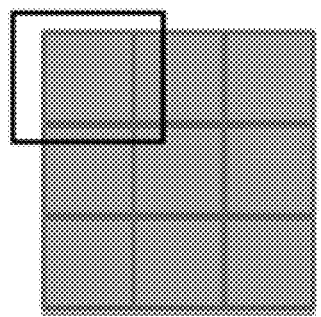
FIGS. 9A-9D show various summing schemes that may be used for calibration and processing.
Figure 9B:
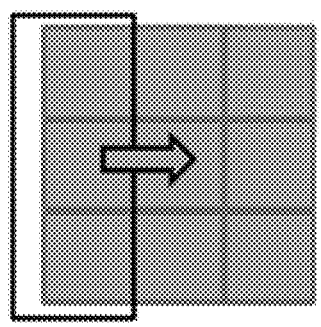
Figure 9C:
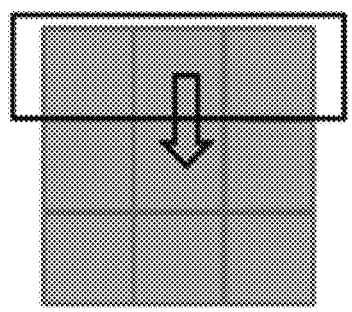
Figure 9D:
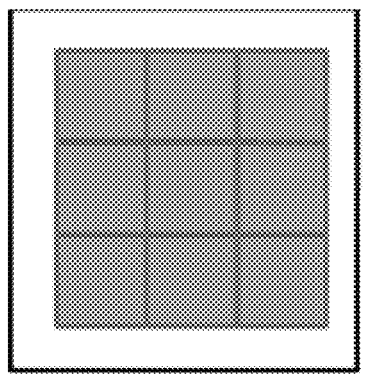

In steps 360S and 360C, final bad pixel criteria will be saved as at least one software table and used in the object scan/processing. Depending on the variation of the analysis results of the calibration scans, there could be multiple bad pixel maps/tables for different scan protocols. FIGS. 4A and 5B show the results of updating an existing spectral bad pixel table with an additional bad pixel for protocol S2 where there was already a bad pixel stored therein for protocol S1. Similarly, FIGS. 5A and 5B show the results of updating an existing counting bad pixel table with an additional bad pixel for protocol C1 where there were already two bad pixels stored therein for protocols C1 and C2. The bad pixel calibration and generation can be performed periodically to make sure the degraded pixels can be captured. The bad pixel map/table will be updated if new bad pixels are identified. In one embodiment, the bad pixel tables are stored only within the system that performs processing (e.g., interpolation) to account for the bad pixels. Alternatively, to increase parallel processing within the system, the detector boards and/or the modules can be fitted with processors to store board-specific or module-specific bad pixel tables. In such a configuration, the detector boards and/or the modules can be programmed at the start of a scan to understand what protocol is being used and to perform the data correction interpolation) according to the protocol locally. In such a configuration, it is further possible to perform any summing (e.g., with respect to FIGS. 9B-9D) at the detector boards and/or the modules to reduce an amount of data that has to be sent from the detector boards and/or the modules to the system. Likewise, it is possible to perform pixel-specific, module-specific, and detector board-specific attenuation correction using similar tables stored within the corresponding module or detector board.

The detector array usually employs a modulated or tiled design, and consists of smaller unit. When applying all the screening criteria, one can get the total number of bad pixels within a detector module. If the number of bad pixels exceed the predefined value, or the bad pixels form a cluster that still impact the image quality with correction, the detector module would be considered bad and require replacement. For example, as shown in FIG. 5B, the counting bad pixel table indicates the beginning of a cluster that may require the replacement of module 16 in detector board 3.

For a small pixelated PCD design, it is possible to use different summing scheme to generate standard resolution and high resolution images as shown in FIGS. 9A-9D. Different summing schemes include, but are not limited to, for a N×N subpixel design, 1×1, or 1×N, or N×1, or N×N (as shown in FIGS. 9A-9D, respectively) as the basic pixel unit in the processing. Then the corresponding bad pixel analysis will follow the same summing scheme and generate the bad pixel map for each scheme respectively. The particular bad pixel map will be used for the object scan processing to determine the pixels to ignore in the scanning process.

In addition, when being used in a summing technique, each bad micro pixel can be identified with respect to the macro pixel to which it belongs, and in each summed macro pixel the bad micro pixel can be excluded in the summation processing. In such configurations, based on the number of bad micro pixels in each macro pixel, the system likewise can maintain a bad macro pixel map to ignore corresponding, macro pixels from being included in future scans. For example, when there is more then 4 out of 9 micro pixels in the same 3×3 macro pixel, that macro pixel is classified as a bad macro pixel (either for a particular type of scanning or regardless of the test results of the other criteria at the macro pixel level, depending on how the system is configured).

Figure 7:
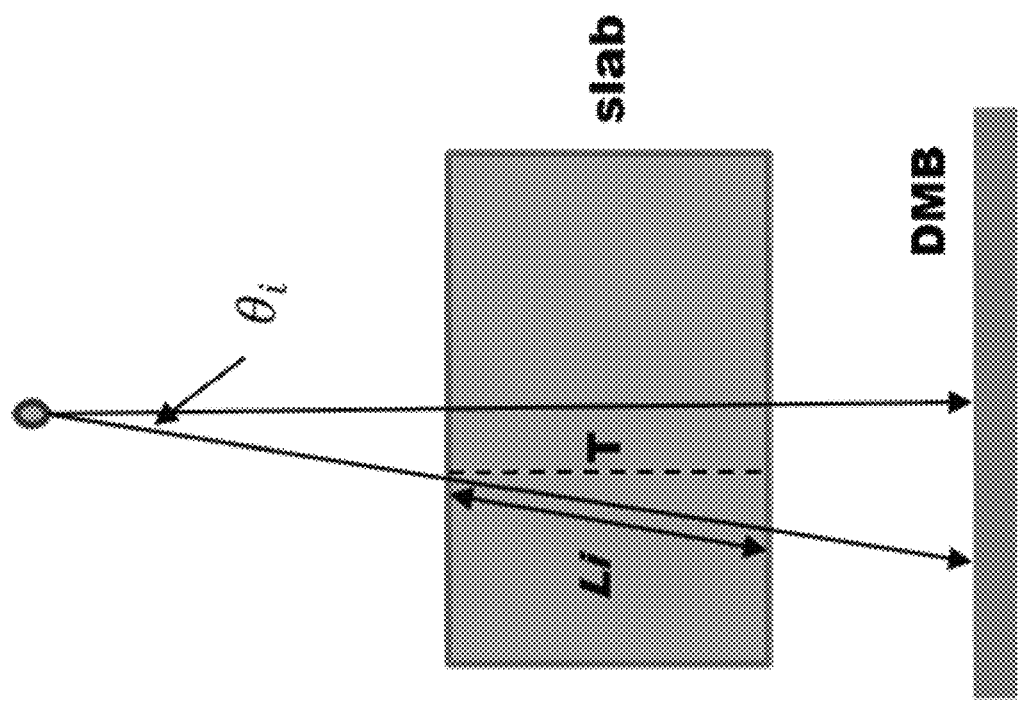
FIG. 7 illustrates calibration slab path lengths at different detector pixels that can be used as part of a series of calibration scans according to one aspect of FIG. 3.

With a typical fan beam coverage in a 3rd generation CT, flat slabs can be used as part of the calibration scans in step 310 with slightly different actual path lengths across the detector array, as shown in FIG. 7. The actual path lengths $L_i$ for each detector pixel of these calibration scans can be calculated by:

$$L_i = T/\cos \theta_i \quad (9)$$

where T is the thickness of the calibration slab, and $\theta_i$ is the projected fan angle of detector pixel i on a detector module blade (DMB), wherein the DMB consists of rows and channels.

Furthermore, calibration with different slabs and thicknesses may be done using a static scan configuration without rotation. The slabs should be large enough to cover the entire detector array and kept well levelled during the entire data acquisition. If for thick slabs, the CT gantry bore size does not allow for a single slab position to cover the entire detector surface, the slab position can be adjusted and multiple scans can be used to cover the entire detector surface. In another embodiment, the calibration with different slabs and thickness may be done using a scan configuration with rotation.

The additional system variations (e.g. tube flux, ASG shadow, etc.) with different rotation speed may be captured by air scans and a reference detector, and corrected accordingly in the air flux term $N_0$ of the forward model. For example, air scans at each rotation speed may be performed prior to the patient/object scan to calibrate the ASG deflection, as well as other beam path variations during rotation that induce the incident flux variation across the detector at different views.

Referring to FIG. 8, the various calibration slabs can be combined together in a direction alone at least a portion of the length of the patient couch to become a long "wedge-like" phantom, so that by moving the position of the couch (or whatever transport mechanism is conveying the slabs), each calibration path length can be detected without re-aligning the Phantom, thereby accelerating the calibration process.

To increase the calibration path length combinations for each slab configuration, the X-ray tube can be positioned at various locations while the slabs are fixed and levelled in the X-Y plane, as illustrated in FIG. 10, which is a schematic showing how multiple tube locations can generate different path lengths for the slab scan in this calibration. As an example, for a given slab thickness T, at detector pixel i, which is located at fan angle $\emptyset_i$, when the tube is placed at different positions ($-\theta$, 0, $\theta$), measured path lengths are given by:

$$L_i(-\theta) = \frac{T}{\cos(x_1)};$$

$$L_i(0) = \frac{T}{\cos(\emptyset)};$$

$$L_i(\theta) = \frac{T}{\cos(x_2)};$$

where $x_1 = \theta - \emptyset$, $x_2 = \theta + \emptyset$. In one embodiment, the typical range of $\emptyset$ could be between 0 to 25 degree, and $\theta$ can be selected between 20 to 60 degrees depending on the slab thickness intervals. By using this park and shoot scheme, it can triple the path length samples for most of the detector channels, hence, greatly reduced the number of calibration slabs needed to cover the same or larger path length range. The tube can also park at more than three positions to farther increase the calibration samples, following the same calculation method described above. For a wide cone coverage system, the calibration path length needs to be calculated based on the projected angle at both the channel and the row direction.

In one embodiment, the slabs are flat and kept levelled during the calibration; this is because it reduces/controls the uncertainty of the path length. In another embodiment, the slabs do not necessarily have to be flat nor level, so long as the path lengths are known and controlled. Further, in one embodiment, each of the slabs are made up of a single material. In another embodiment, the slabs do not always have to consist of a single material. For example, a slab could comprise multiple materials. Examples of materials for a slab can include polypropylene, water, aluminium, titanium/copper, tissue surrogates, other polymers, stainless steel or other metals, k-edge materials, and various tissue mimicking materials.

The at least one slab can also be laid out in a variety of ways to obtain multiple pathlengths from one or more materials. For instance, multiple slabs can be lined up adjacently along the patient couch for scanning as the patient couch moves within a radiography gantry. The multiple slabs can be of the same height with multiple materials, multiple heights with the same material, or a multiple heights with multiple materials. In another exemplary embodiment, slabs can be held and suspended in the CT apparatus field of vision (e.g. using a robotic arm). In another exemplary embodiment, multiple slabs can be lined up with a shift in z-direction between each two adjacent slabs. As the slabs move in and out of the scanning field of vision, multiple stepwise pathlength data can be acquired continuously.

Figure 11:
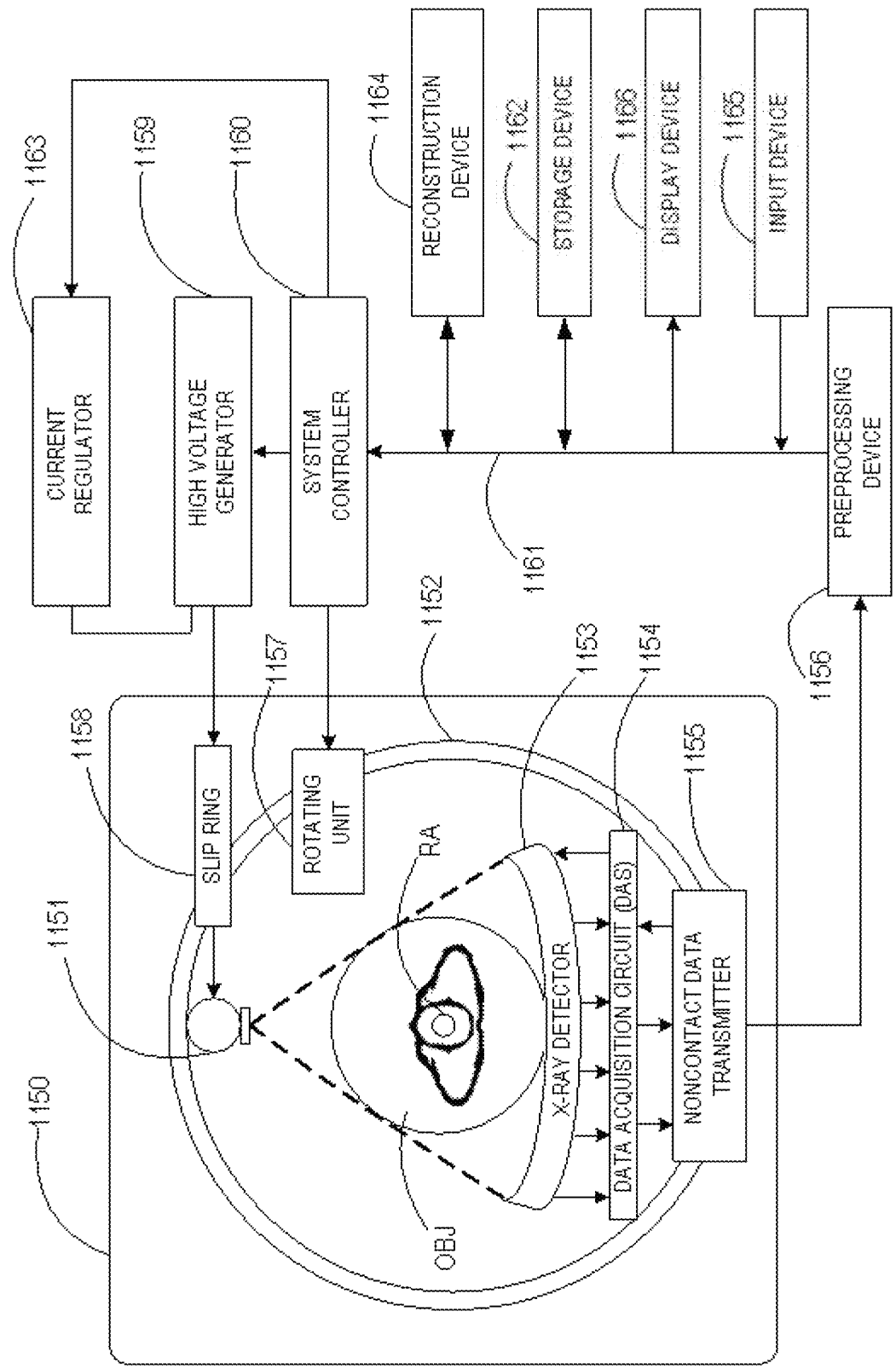
FIG. 11 shows a CT scanner system that can incorporate the techniques disclosed herein.

It can be appreciated that, in one embodiment, the above mentioned techniques can be applied to a CT apparatus or scanner. FIG. 11 illustrates an implementation of a horizontal radiography gantry included in a CT apparatus or scanner. As shown in FIG. 11, a radiography gantry 1150 (illustrated from a side view) includes an X-ray tube 1151, an annular frame 1152, and a multi-row or two-dimensional-array type X-ray detector 1153. The X-ray tube 1151 and X-ray detector 1153 are diametrically mounted across an object OBJ (e.g., a patient) on the annular frame 1152, which is rotatably supported around a rotation axis RA. A rotating unit 1157 rotates the annular frame 1152 at a high speed, such as 0.4 sec/rotation, while the object OBJ (e.g., a patient) is being moved along the axis RA into or out of the illustrated page.

An embodiment of an X-ray CT apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate-type, which is currently the mainstream, will be exemplified.

The multi-slice X-ray CT apparatus further includes a high voltage generator 1159 that generates a tube voltage applied to the X-ray tube 1151 through a slip ring 1158 so that the X-ray tube 1151 generates X-rays. An X-ray detector 1153 is located at an opposite side from the X-ray tube 1151 across the object OBJ (e.g., a patient) for detecting the emitted X-rays that have transmitted through the object OBJ (e.g., a patient). The X-ray detector 1153 further includes individual detector elements or units and may be a photon-counting detector. In the fourth-generation geometry system, the X-ray detector 1153 may be one of a plurality of detectors arranged around the object OBJ (e.g., a patient) in a 360° arrangement.

The CT apparatus further includes other devices for processing the detected signals from the X-ray detector 1153. A data acquisition circuit or a Data Acquisition System (DAS) 1154 converts a signal output from the X-ray detector 1153 for each channel into a voltage signal, amplifies the signal, and further converts the signal into a digital signal. The X-ray detector 1153 and the DAS 1154 are configured to handle a predetermined total number of projections per rotation (TPPR).

The above-described data is sent to a preprocessing device 1156, which is housed in a console outside the radiography gantry 1150 through a non-contact data transmitter 1155. The preprocessing device 1156 performs certain corrections, such as sensitivity correction, on the raw data. A memory 1162 stores the resultant data, which is also called projection data at a stage immediately before reconstruction processing. The memory 1162 is connected to a system controller 1160 through a data/control bus 1161, together with a reconstruction device 1164, input device 1165, and display 1166. The system controller 1160 controls a current regulator 1163 that limits the current to a level sufficient for driving the CT system. In an embodiment, the system controller 1160 implements optimized scan acquisition parameters, as described above. The reconstruction device 1164 can include circuitry configured to perform the above mentioned techniques, such as method 600.

The method and system described herein can be implemented in a number of technologies but generally relate to imaging devices and/or processing circuitry for performing the techniques described herein. In one embodiment, the processing circuitry is implemented as one of or as a combination of: an application specific integrated circuit (ASIC), a field programmable gate array (FPGA), a generic array of logic (GAL), a programmable array of logic (PAL), circuitry for allowing one-time programmability of logic gates (e.g., using fuses) or reprogrammable logic gates. Furthermore, the processing circuitry can include computer processor circuitry having embedded and/or external non-volatile computer readable memory (e.g., RAM, SRAM, FRAM, PROM, EPROM, and/or EEPROM) that stores computer instructions (binary executable instructions and/or interpreted computer instructions) for controlling the computer processor to perform the processes described herein. The computer processor circuitry may implement a single processor or multiprocessors, each supporting a single thread or multiple threads and each having a single core or multiple cores.

Embodiments of the present disclosure may also be as set forth in the following, parentheticals.

(1) A method of determining an underperforming pixel in a small pixelated photon counting detector computed tomography (CT) system, including, but not limited to: (a) performing plural in-situ calibration scans using the CT system; (b) determining at least one pixel of at least one detector of the CT system is underperforming according to a first set of criteria based on a counting image and a spectral image both generated by the plural calibration scans; and (c) storing an indication of the at least one pixel of the at least one detector of the CT system determined to be underperforming in a map of underperforming pixels.

(2) The method of (1), wherein performing plural in-situ calibration scans using the CT system includes, but is not limited to, performing at least one of (a) plural air scans at different intensities, (b) plural scans with different attenuation path lengths, (c) a dark scan without X-ray to measure counting background, (d) a noise scan, and (e) plural repeatability and/or reliability scans.

(3) The method of any one of (1)-(2), wherein determining that the at least one pixel of the at least one detector of the CT system is underperforming includes, but is not limited to, determining whether the scans are consistent with a calibrated forward model.

(4) The method of any one of (1)-(3), wherein determining that the at least one pixel of the at least one detector of the CT system is underperforming according to the first set of criteria includes, but is not limited to: (b1) determining that the plural calibration scans indicate that the at least one pixel of at least one detector of the CT system is underperforming according to the first set of criteria; (b2) generating a second set of criteria different from the first set of criteria; and (b3) determining that the plural calibration scans indicate that the at least one pixel of the at least one detector of the CT system is underperforming according to the second set of criteria.

(5) The method of any one of (1)-(4), wherein performing plural in-situ calibration scans using the CT system includes, but is not limited to, performing scans using a calibration phantom.

(6) The method of any one of (1)-(5), wherein determining if the plural calibration scans indicate that at least one pixel of at least one detector of the CT system is underperforming according, to the first set of criteria includes, but is not limited to: reconstructing an image using the first set of criteria; and determining if the reconstructed image includes rings created by the at least one pixel of at least one detector of the CT system that is underperforming.

(7) The method of any one of (1)-(6), wherein storing the indication of the at least one pixel of at least one detector of the CT system determined to be underperforming includes, but is not limited to, storing the indication in a corresponding one of a bad spectral pixel table and a bad counting pixel table.

(8) The method of (7), wherein storing the indication of the at least one pixel of the at least one detector of the CT system determined to be underperforming comprises storing in the bad counting pixel table that the at least one pixel of the at least one detector of the CT system determined to be underperforming experienced any combination of at least one of (1) an excessive background count rate, (2) a count rate that is too high at a given flux, (3) a count rate that is too low at a given flux, (4) a ratio of counting variation to mean value of counts greater than a first threshold, and (5) a deviation from a count mean greater than a second threshold.

(9) The method of any one of (1)-(8), wherein storing the indication of the at least one pixel of at least one detector of the CT system determined to be underperforming includes, but is not limited to, storing a protocol for which the at least one pixel of at least one detector of the CT system is determined to be underperforming.

(10) The method of any one of (1)-(9), wherein performing plural in-situ calibration scans using the CT system includes, but is not limited to, performing in-situ calibration scans periodically to determine detector performance inconsistence in the time domain.

(11) The method of any one of (1)-(10), further including, but not limited to, performing count-based scanning of an object using the CT system without using the at least one pixel of the at least one detector.

(12) The method of any one of (1)-(10), further including, but not limited to, performing spectral-based scanning of an object using the CT system without using the at least one pixel of the at least one detector.

(13) The method of (9), further including, but not limited to: performing scanning of an object using the CT system without using the at least one pixel of the at least one detector for the protocol for which the at least one pixel of at least one detector of the CT system is determined to be underperforming and performing scanning of the object using the CT system using the at least one pixel of the at least one detector for protocols other than the protocol for which the at least one pixel of at least one detector of the CT system is determined to be underperforming.

(14) The method of any one of (1)-(13), further including, but not limited to, performing scanning of an object using the CT system by summing values from a macroblock including the at least one pixel of the at least one detector without using the at least one pixel of the at least one detector as part of a result of the summing.

The method of (7), wherein storing the indication of the at least one pixel of the at least one detector of the CT system determined to be underperforming comprises storing in the bad spectral pixel table that the at least one pixel of the at least one detector of the CT system determined to be underperforming experienced any combination of at least one of: (1) a corresponding normalized bin count being above a maximum threshold and (2) a corresponding normalized bin count being below a minimum threshold.

(16) A computed tomography (CT) system, including, but not limited to: processing circuitry configured to perform the methods of any one of (1)-(15).

(17) A computer system including a computer readable medium for storing computer executable instructions to control a computer processor, under control of the stored computer executable instructions, to perform the methods of any one of (1)-(15).

Numerous modifications and variations of the embodiments presented herein are possible in light of the above teachings. It is therefore to be understood that within the scope of the claims, the disclosure may be practiced otherwise than as specifically described herein.

The invention claimed is:

1. A method of determining an underperforming pixel in a small pixelated photon counting detector computed tomography (CT) system, comprising:
   performing plural in-situ calibration scans using the CT system;
   determining at least one pixel of at least one detector of the CT system is underperforming according to a first set of criteria based on a counting image and a spectral image both generated by the plural calibration scans; and
   storing an indication of the at least one pixel of the at least one detector of the CT system determined to be underperforming in a map of underperforming pixels, wherein
   determining that the at least one pixel of the at least one detector of the CT system is underperforming according to the first set of criteria comprises:
      determining that the plural calibration scans indicate that the at least one pixel of the at least one detector of the CT system is underperforming according to the first set of criteria;
      generating a second set of criteria different from the first set of criteria; and
      determining that the plural calibration scans indicate that the at least one pixel of the at least one detector of the CT system is underperforming according to the second set of criteria.

2. The method as claimed in claim 1, wherein performing plural in-situ calibration scans using the CT system comprises performing at least one of (a) plural air scans at different intensities, (b) plural scans with different attenuation path lengths, (c) a dark scan without X-ray to measure counting background, (d) a noise scan, and (e) plural repeatability and/or reliability scans.

3. The method as claimed in claim 1, wherein determining that the at least one pixel of at least one detector of the CT system is underperforming comprises determining whether the scans are consistent with a calibrated forward model.

4. The method as claimed in claim 1, wherein performing plural in-situ calibration scans using the CT system comprises performing scans using a calibration phantom.

5. The method as claimed in claim 1, wherein determining if the plural calibration scans indicate that at least one pixel of at least one detector of the CT system is underperforming according to the first set of criteria comprises:
   reconstructing an image using the first set of criteria; and
   determining if the reconstructed image includes rings created by the at least one pixel of at least one detector of the CT system that is underperforming.

6. The method as claimed in claim 1, wherein storing the indication of the at least one pixel of the at least one detector of the CT system determined to be underperforming comprises storing the indication in a corresponding one of a bad spectral pixel table and a bad counting pixel table.

7. The method as claimed in claim 6, wherein storing the indication of the at least one pixel of the at least one detector of the CT system determined to be underperforming comprises storing in the bad counting pixel table that the at least one pixel of the at least one detector of the CT system determined to be underperforming experienced any combination of at least one of: (1) an excessive background count rate, (2) a count rate that is too high at a given flux, (3) a count rate that is too low at a given flux, (4) a ratio of counting variation to mean value of counts greater than a first threshold, and (5) a deviation from a count mean greater than a second threshold.

8. The method as claimed in claim 6, wherein storing the indication of the at least one pixel of the at least one detector of the CT system determined to be underperforming comprises storing in the bad spectral pixel table that the at least one pixel of the at least one detector of the CT system determined to be underperforming experienced any combination of at least one of: (1) a corresponding normalized bin count being above a maximum threshold and (2) a corresponding normalized bin count being below a minimum threshold.

9. The method as claimed in claim 1, wherein storing the indication of the at least one pixel of the at least one detector of the CT system determined to be underperforming comprises storing a protocol for which the at least one pixel of the at least one detector of the CT system is determined to be underperforming.

10. The method as claimed in claim 9, further comprising:
performing scanning of an object using the CT system without using the at least one pixel of the at least one detector for the protocol for which the at least one pixel of at least one detector of the CT system is determined to be underperforming; and
performing scanning of the object using the CT system using the at least one pixel of the at least one detector for protocols other than the protocol for which the at least one pixel of at least one detector of the CT system is determined to be underperforming.

11. The method as claimed in claim 1, wherein performing plural in-situ calibration scans using the CT system comprises performing in-situ calibration scans periodically to determine detector performance inconsistence in the time domain.

12. The method as claimed in claim 1, further comprising performing count-based scanning of an object using the CT system without using the at least one pixel of the at least one detector.

13. The method as claimed in claim 1, further comprising performing spectral-based scanning of an object using the CT system without using the at least one pixel of the at least one detector.

14. The method as claimed in claim 1, further comprising performing scanning of an object using the CT system by summing values from a macroblock including the at least one pixel of the at least one detector without using the at least one pixel of the at least one detector as part of a result of the summing.

15. A computed tomography (CT) system, comprising:
processing circuitry configured to:
perform plural in-situ calibration scans using the CT system;
determine at least one pixel of at least one detector of the CT system is underperforming according to a first set of criteria based on a counting image and a spectral image both generated by the plural calibration scans; and
store an indication of the at least one pixel of the at least one detector of the CT system determined to be underperforming in a map of underperforming pixels, wherein
the processing circuitry is configured to determine that the at least one pixel of the at least one detector of the CT system is underperforming by:
determining that the plural calibration scans indicate that the at least one pixel of the at least one detector of the CT system is underperforming according to the first set of criteria;
generating a second set of criteria different from the first set of criteria; and
determining that the plural calibration scans indicate that the at least one pixel of the at least one detector of the CT system is underperforming according to the second set of criteria.

16. The system as claimed in claim 15, wherein the processing circuitry configured to perform plural in-situ calibration scans using the CT system comprises processing circuitry configured to perform at least one of (a) plural air scans at different intensities, (b) plural scans with different attenuation path lengths, (c) a dark scan without X-ray to measure counting background, (d) a noise scan, and (e) plural repeatability and/or reliability scans.

17. The system as claimed in claim 15, wherein the processing circuitry further comprises processing circuitry configured to perform scanning of an object using the CT system without using the at least one pixel of the at least one detector.

18. The system as claimed in claim 15, wherein the processing circuitry configured to store the indication of the at least one pixel of the at least one detector of the CT system determined to be underperforming comprises processing circuitry configured to store a protocol for which the at least one pixel of the at least one detector of the CT system is determined to be underperforming.

19. The system as claimed in claim 18, wherein the processing circuitry is further configured to:
perform scanning of an object using the CT system without using the at least one pixel of the at least one detector for the protocol for which the at least one pixel of at least one detector of the CT system is determined to be underperforming; and
perform scanning of the object using the CT system using the at least one pixel of the at least one detector for protocols other than the protocol for which the at least one pixel of at least one detector of the CT system is determined to be underperforming.

20. The system as claimed in claim 15, wherein the processing circuitry is further configured to perform scanning of an object using the CT system by summing values from a macroblock including the at least one pixel of the at least one detector without using the at least one pixel of the at least one detector as part of a result of the summing.

21. A method of determining an underperforming pixel in a small pixelated photon counting detector computed tomography (CT) system, comprising:
performing plural in-situ calibration scans using the CT system;
determining at least one pixel of at least one detector of the CT system is underperforming according to a first set of criteria based on a counting image and a spectral image both generated by the plural calibration scans; and storing an indication of the at least one pixel of the at least one detector of the CT system determined to be underperforming in a map of underperforming pixels, wherein storing the indication of the at least one pixel of the at least one detector of the CT system determined to be underperforming comprises storing the indication in a corresponding one of a bad spectral pixel table and a bad counting pixel table.

\* \* \* \* \*